United States Patent [19]
Parks

[11] Patent Number: 6,094,751
[45] Date of Patent: Aug. 1, 2000

[54] GOGGLE WITH REPLACEABLE SEAL

[75] Inventor: Gerald R. Parks, Chula Vista, Calif.

[73] Assignee: John R. Gregory, Chula Vista, Calif.

[21] Appl. No.: 09/114,423

[22] Filed: Jul. 13, 1998

[51] Int. Cl.[7] ........................................ A61F 9/02
[52] U.S. Cl. ............................................... 2/431
[58] Field of Search ....................... 2/440, 426, 427, 2/428, 430, 431, 432, 436, 437, 439, 441, 446, 447, 9

[56] References Cited

U.S. PATENT DOCUMENTS

| | | | |
|---|---|---|---|
| 1,306,357 | 6/1919 | Shindel | 2/439 |
| 4,955,087 | 9/1990 | Perez et al. | 2/426 X |
| 5,689,834 | 11/1997 | Wilson | 2/441 X |
| 5,867,841 | 2/1999 | Chiang | 2/436 |

*Primary Examiner*—Peter Nerbun
*Attorney, Agent, or Firm*—Henri J. A. Charmasson; John D. Buchaca

[57] ABSTRACT

A goggle having a close fitting interface with the wearer's brow, cheekbones and nose bridge, comprises a set of detachable foam strips for easy and rapid substitution or replacement. Foam strips of various thickness and density are permanently bonded to a carrier band removably attachable to inner portions of the goggle frame.

8 Claims, 2 Drawing Sheets

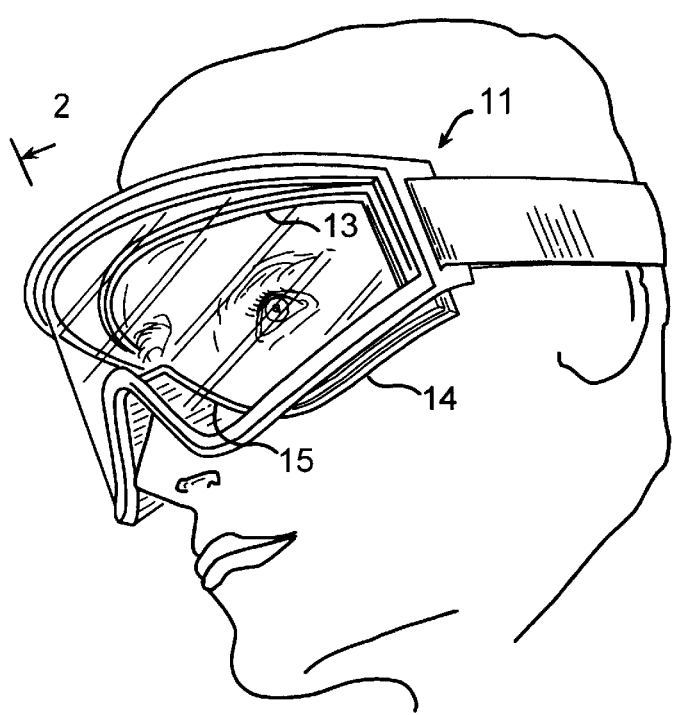
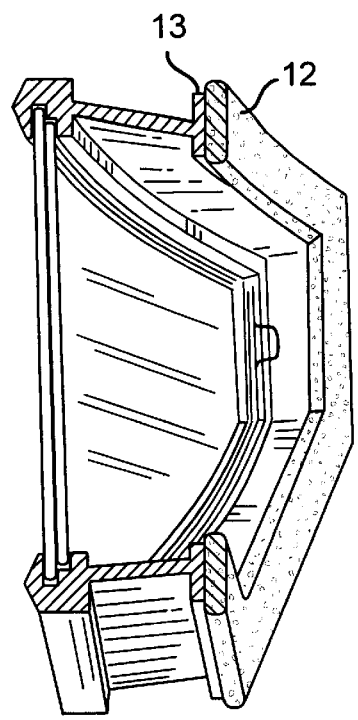
Prior Art
FIG. 1
Prior Art
FIG. 2

GOGGLE WITH REPLACEABLE SEAL

FIELD OF THE INVENTION

This invention relates to protective goggles, and more specifically to goggles requiring a tight fit between the inner side of the frame and the face of the wearer such as goggles worn by skiers, swimmers, motor-cyclists, and paint-ball war game enthusiasts.

BACKGROUND OF THE INVENTION

The above-listed types of goggles require that one or more strips of spongy material such as a synthetic foam be applied along the portions of the goggle frame that come in contact with the wearer's brow, nose bridge and cheekbones. The foam strips act as a perspiration barrier and blotter, and prevent entry of dust, snow, rain water, or debris in the space between the lens and the eye. In the course of intense or lengthy physical activity, the foam strips may become saturated or may collapse, and no longer fulfill their intended purpose. Since, in the prior art, the foam strips were permanently bonded to the frame, the entire goggle had to be discarded and replaced.

The great disparities in the facial features of goggle wearers make it difficult for a manufacturer to offer models that closely fit everybody. The interfacing foam strips provide a limited way to compensate for those disparities. Certain manufacturers have resorted to offering series of the same goggle permanently equipped with foam strips of various sizes and densities.

SUMMARY OF THE INVENTION

The principal and secondary objects of the instant invention are to provide a goggle that can be conveniently customized by offering several types and sizes of interface foam strips between the inner face of the goggle and the particular facial outline of the wearer; and to allow for rapid replacement of worn or saturated foam strips in the course of an intense physical activities without having to discard an entire goggle assembly, while at the same time minimizing production costs.

These and other valuable objects are achieved by permanently mounting foam strips of various types, thickness and densities on carrier bands that can be quickly and detachably secured against the inner face of a versatile goggle assembly.

BRIEF DESCRIPTION OF THE DRAWING

FIG. 1 is a perspective view of a person wearing a goggle of the prior art;

FIG. 2 is perspective, cross-sectional view of a goggle of the prior art taken along line 2—2 of FIG. 1;

DESCRIPTION OF THE PREFERRED EMBODIMENT OF THE INVENTION

Figure 3:
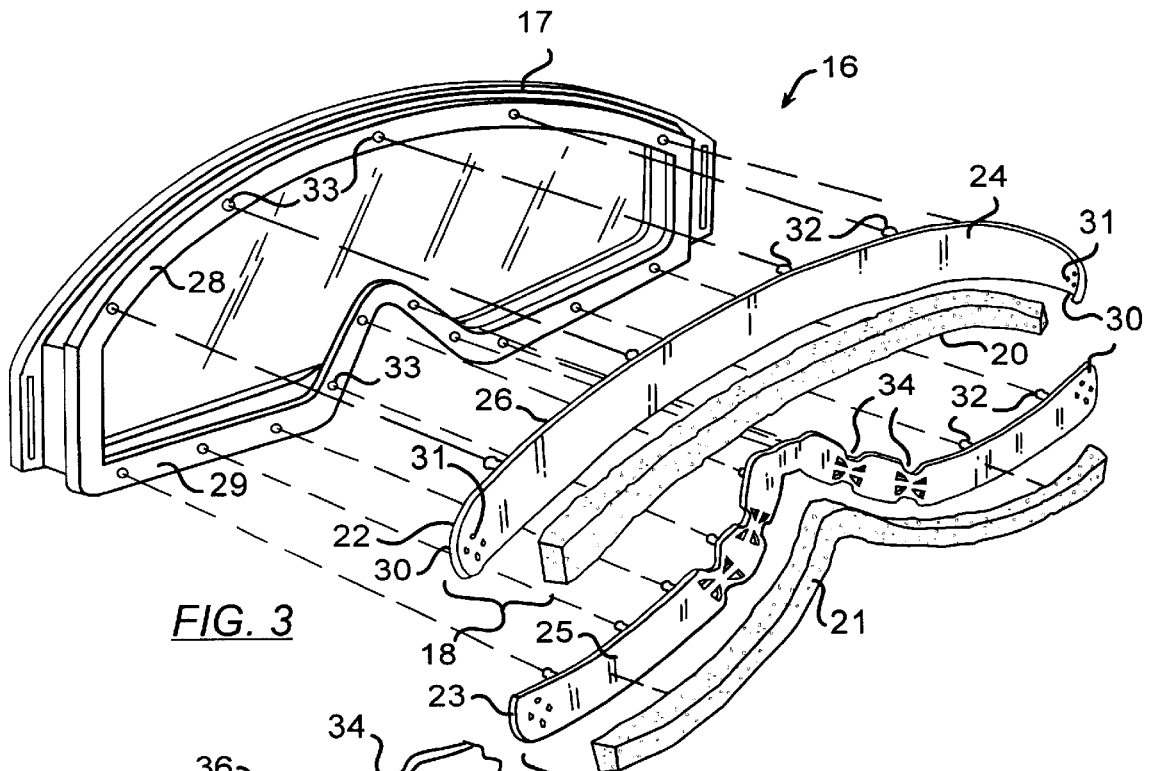
FIG. 3 is an exploded perspective view of a goggle assembly according to the invention.

Referring now to the drawing, there is illustrated in FIGS. 1 and 2 a goggle assembly 11 representative of the prior art. It must be noted that a strip 12 of perspiration blotting spongy foam material is permanently bonded against the brow section 13 of the inner side of the goggle frame. Another similar strip is also permanently bonded against those sections of the frame that come into contact with the cheekbone 14 and nose bridge 15 areas. The type, thickness and density of the foam strips are preferably selected according to the purpose and utility of the goggle, and the requirements of the prospective buyers. Accordingly goggles must be manufactured and offered with different foam strip characteristics.

Figure 4:
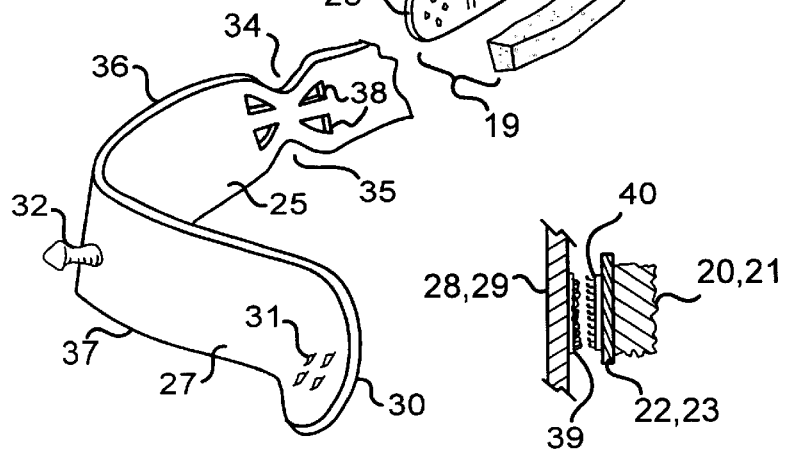
FIG. 4 is a detail perspective view of a section of one of the carrier strip.
Figure 5:
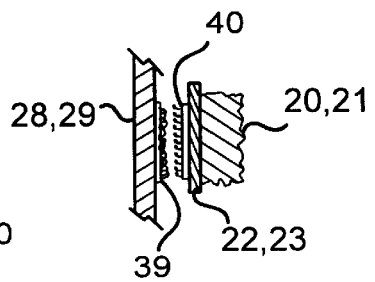
FIG. 5 is a cross-sectional view of an alternate fastener for the carrier strip.

In the embodiment 16 of the invention illustrated in FIGS. 3–5, a universal type of frame 17 is used and equipped with a set of a choice of substitutable foam barriers 18, 19. Each foam barrier comprises a strip 20, 21 of spongy material, and a carrier strip 22, 23. Each carrier strip consist of a band of synthetic material having an inner face 24, 25 against which the strip of spongy material is permanently bonded. The opposite outer face 26, 27 of the carrier strip can be detachably secured to one of the flanges 28, 29 on the inner side of the goggle. The upper flange 28 forms a brow portion of the goggle frame which rest against the brow of the wearer. The lower flange 28 forms a cheek-and nose section which comes in contact with the wearer's cheekbone and nose bridge areas. Each carrier strip 22, 23 is generally commensurate with, i.e., has about the same length as the frame section against which it is mounted, and includes at each of its opposite longitudinal ends a short end segment 30 free of spongy material having a series of bumps 31 or other type of asperities that facilitate the grabbing and holding of the carrier strip during installation.

In a first type of detachable interconnection between the carrier strips and the frame best illustrated in FIG. 4, small nibs 32 projecting from and perpendicularly to the outer faces 26, 27 of the strip carrier are engaged into corresponding and symmetrically positioned bores 33 in the corresponding flange.

The bore diameter is commensurate with the shaft diameter of the nibs to assure stable engagement. The slight resiliency of the synthetic material used in the fabrication of the frame and carrier strip allows for easy removal of the foam barriers and the installment of a substitute one.

In order to provide some degree of transversal flexibility to the carrier strip 23 mounted against the cheekbone and nose bridge portion of the frame, pairs of indentations 34, 35 are cut into longitudinal edges 36, 37. The indentations are located in the portions of the carrier strip that need to bend around the nose bridge area. Additional flexibility is provided by a series of small apertures 38 cut through the thickness of the carrier strip and between the sets of indentations 35, 36.

The indentation/aperture combination provides enhanced flexibility in adapting the strip to various goggle shapes and sizes while maintaining the strength and durability of the carrier strip and ease of manufacture.

In a second type of interconnection between each carrier strip and the frame a two interconnecting part type of fastener is used as illustrated in FIG. 5. For instance, a first band 39 of loop-type fabric fastener is permanently bonded to the frame flange 28, 29. A second band 40 of hook-type fabric fastener is permanently bonded to the outer face of the strip carrier 22, 23.

Other types of fasteners or a tacky and breakable adhesive bond may also be used, and would constitute obvious equivalent means to form a detachable bond.

While the preferred embodiments of the invention have been described, modifications can be made and other embodiments may be devised without departing from the spirit of the invention and the scope of the appended claims.

What is claimed is:

1. A goggle which comprises:

a frame including a brow portion shaped and dimensioned to bear against the brow of a wearer;

a first carrier strip commensurate with said brow portion, and having a outer face detachably secured to said brow portion and an opposite inner face;

a strip of perspiration-blotting spongy material bonded to said inner face; and interconnecting structures between said carrier strip and said frame, said structures being shaped and dimensioned for rapid and easy attachment and detachment of said carrier strip to and from said frame.

2. The goggle of claim 1 wherein:

said means for detachably securing comprise a plurality of nibs projecting from the outer face of said carrier strip; and said brow portion has a plurality of bores positioned, shaped and dimensioned to intimately engage said nibs.

3. The goggle of claim 1 wherein:

said means for detachably securing comprise a plurality of fasteners each having two separable interconnecting parts, one of said parts being attached to said brow portion, the other of said part being attached to the outer face of said carrier strip.

4. The goggle of claim 1 wherein:

said frame further comprises a cheek-and-nose section shaped, dimensioned and positioned to bear against the cheekbones and nose bridge of a wearer; and said goggle further comprises a second carrier strip commensurate with said cheek-and-nose section, and having an outer face detachably secured to said cheek-and-nose section, and an opposite inner face;

and a second strip of spongy material bonded to said inner face.

5. A goggle which comprises:

a frame including a brow portion shaped and dimensioned to bear against the brow of a wearer;

a first carrier strip commensurate with said brow portion, and having a outer face detachably secured to said brow portion and an opposite inner face;

a strip of spongy material bonded to said inner face;

wherein said frame further comprises a cheek-and-nose section shaped, dimensioned and positioned to bear against the cheekbones and nose bridge of a wearer; and said goggle further comprises a second carrier strip commensurate with said cheek-and-nose section, and having an outer face detachably secured to said cheek-and-nose section, and an opposite inner face;

and a second strip of spongy material bonded to said inner face;

wherein said second carrier strip comprises:

a flexible band of synthetic material having a given width and a said band further having sets of cooperating and opposite pairs of indentations along said edges;

said pairs of indentations being positioned along said edges to increase transversal flexibility in said band at locations generally corresponding to base and apex sections of said nose bridge.

6. The goggle of claim 5 wherein said band further has at least one aperture between each of said pairs of indentations.

7. A goggle which comprises:

a frame including a brow portion shaped and dimensioned to bear against the brow of a wearer;

a first carrier strip commensurate with said brow portion, and having a outer face detachably secured to said brow portion and an opposite inner face;

a strip of spongy material bonded to said inner face;

wherein said first carrier strip further comprises surface asperities at opposite longitudinal end portions of thereof.

8. The goggle of claim 4 wherein said second carrier strip further comprises surface asperities at opposite longitudinal end portions thereof.

* * * * *